United States Patent
Kim

(10) Patent No.: US 10,426,580 B2
(45) Date of Patent: Oct. 1, 2019

(54) IMPLANT UNIT

(71) Applicant: Kwang Seob Kim, Fullerton, CA (US)

(72) Inventor: Kwang Seob Kim, Fullerton, CA (US)

(*) Notice: Subject to any disclaimer, the term of this patent is extended or adjusted under 35 U.S.C. 154(b) by 0 days.

(21) Appl. No.: 15/002,597

(22) Filed: Jan. 21, 2016

(65) Prior Publication Data

US 2016/0206409 A1 Jul. 21, 2016

(30) Foreign Application Priority Data

Jan. 21, 2015 (KR) ........................ 10-2015-0010144
Oct. 29, 2015 (KR) ........................ 10-2015-0151082

(51) Int. Cl.
*A61C 8/00* (2006.01)

(52) U.S. Cl.
CPC .......... *A61C 8/0078* (2013.01); *A61C 8/0062* (2013.01); *A61C 8/0068* (2013.01)

(58) Field of Classification Search
CPC ........ A61C 8/0078; A61C 8/006–0063; A61C 8/0069; A61C 8/0068; A61C 8/0054; A61C 8/0086; A61C 8/0057; A61C 8/005
See application file for complete search history.

(56) References Cited

U.S. PATENT DOCUMENTS

| | | | | |
|---|---|---|---|---|
| 4,324,550 A * | 4/1982 | Reuther | ............... | A61C 8/0022 433/169 |
| 4,957,437 A * | 9/1990 | Shimura | ............... | A61C 8/005 433/169 |
| 5,026,285 A * | 6/1991 | Durr | ...................... | A61C 8/005 433/141 |
| 5,049,073 A * | 9/1991 | Lauks | .................. | A61C 8/0018 433/169 |
| 5,092,771 A * | 3/1992 | Tatum, III | ............ | A61C 8/0018 433/173 |
| 5,213,500 A * | 5/1993 | Salazar | ................ | A61C 8/0018 433/169 |
| 5,468,150 A * | 11/1995 | Brammann | ............ | A61C 8/005 433/169 |
| 5,725,377 A * | 3/1998 | Lemler | ................ | A61C 8/0006 433/173 |
| 5,782,918 A * | 7/1998 | Klardie | .................. | A61C 8/005 433/172 |
| 5,888,218 A * | 3/1999 | Folsom | ................ | A61C 8/0018 433/172 |
| 6,726,480 B1 * | 4/2004 | Sutter | .................. | A61C 8/0001 433/173 |

(Continued)

FOREIGN PATENT DOCUMENTS

JP 01-214360 8/1989
KR 10-2008-0049378 6/2008

(Continued)

*Primary Examiner* — Wade Miles
*Assistant Examiner* — Shannel N Wright

(57) ABSTRACT

Provided is an implant unit. The implant unit includes a fixture, which is assembled to an alveolar bone and includes a long hole formed in the depth-wise direction and having an opening on the top of the fixture; an intermediate structure, which is inserted to the long hole via the opening of the fixture; and an abutment assembled to the intermediate structure, wherein a first structure for coupling the fixture to the intermediate structure is formed on the inner surface of the fixture.

6 Claims, 7 Drawing Sheets

(56) References Cited

U.S. PATENT DOCUMENTS

| | | | |
|---|---|---|---|
| 6,743,018 B1* | 6/2004 | Morrow | A61C 8/005 411/55 |
| 2011/0123951 A1* | 5/2011 | Lomicka | A61C 8/0012 433/174 |

FOREIGN PATENT DOCUMENTS

| KR | 10-2013-0073729 | 7/2013 |
|---|---|---|
| KR | 10-2013-0117174 | 10/2013 |

* cited by examiner

IMPLANT UNIT

CROSS-REFERENCE TO RELATED APPLICATION

This application claims priority of Korean Patent Application No. 10-2015-0010144, filed on Jan. 21, 2015 and priority of Korean Patent Application No. 10-2015-0151082, filed on Oct. 29, 2015, in the KIPO (Korean Intellectual Property Office), the disclosure of which is incorporated herein entirely by reference.

BACKGROUND OF THE INVENTION

Field of the Invention

Embodiments of the present disclosure relate to an implant unit, and more particularly, to a dental implant unit capable of reducing stress.

Description of the Related Art

An artificial tooth is an artificially fabricated tooth that is almost identical a natural tooth of a man in terms of the appearance and functions. The artificial tooth is used to replace a natural tooth when the natural tooth is damaged or missing based on various causes, such as a cavity.

In case of replacing a natural tooth with the artificial tooth based on symptoms and prognosis of odontopathies, there are three common approaches including a bridge, a denture, and an implant into an alveolar bone. In case of the bridge, it is necessary to drill healthy adjacent teeth. As a result, natural teeth are damaged. Furthermore, masticating force is weakened due to lack of a dental root, and lifespan thereof is only about ten years. In case of the denture, natural teeth are damaged and the alveolar bone is gradually absorbed. Furthermore, the denture may be detached from the mouth of a user or may irritate the mount of the user.

Meanwhile, an implant surgery for implanting an artificial tooth to the alveolar bone does not damage adjacent natural teeth and may be independently implanted as long as the alveolar bone maintains a suitable condition for the implant surgery. Furthermore, after the implant surgery, the appearance and functions of the artificial tooth are excellent and hardly distinguishable from natural teeth. Therefore, implant surgeries are being widely performed. Furthermore, an implant unit used for the implant surgeries may be permanently used with proper cares.

A conventional implant unit for implanting an artificial tooth to the alveolar bone generally includes a crown that functions as a tooth, a fixture functions as a dental root, and an abutment interconnecting the crown and the fixture. In case of the implant unit, when weights are continuously applied in the mouth as a user masticates the food, the alveolar bone may be damaged or the alveolar bone may be absorbed due to continuous stress concentration, thereby causing additional odontopathies or reducing lifespan of the implant unit. Furthermore, if the alveolar bone is already significantly absorbed, it is difficult or impossible to apply a conventional implant unit without performing an additional bone grafting surgery, e.g., a case where a distance to a paranasal sinus (maxillary sinus) at the maxillary molar is insufficient or a case where a distance to a nerve at the mandible molar is insufficient.

SUMMARY OF THE INVENTION

Embodiments of the present invention include an implant unit that is capable of reducing possible continuous stress to the implant unit for permanent use of the implant unit and prevention of additional odontopathies due to the implant unit.

According to an aspect of the inventive concept, there is provided an implant unit including a fixture, which is assembled to an alveolar bone and includes a long hole formed in the depth-wise direction and having an opening on the top of the fixture; an intermediate structure, which is inserted to the long hole via the opening of the fixture; and an abutment assembled to the intermediate structure, wherein a first structure for coupling the fixture to the intermediate structure is formed on the inner surface of the fixture.

A second structure for coupling the intermediate structure to the fixture may be formed on the outer surface of the intermediate structure. At least one of the first structure and the second structure may include a screw thread pattern.

The long hole of the fixture may include a bottom surface, and a gap may be formed between the bottom surface of the fixture and a bottom surface of the intermediate structure.

The long hole of the fixture may include a first lower inclined surface, and the intermediate structure may include a second lower inclined surface. The second lower inclined surface may include a groove.

The fixture may include an accommodating surface connected to the upper portion of the first lower inclined surface and having the first structure, and the intermediate structure may include an extension surface connected to the upper portion of the second lower inclined surface and having the second structure for coupling the intermediate structure to the fixture. The fixture may include a first upper inclined surface connected to the upper portion of the accommodating surface, and the intermediate structure may include a second upper inclined surface connected to the upper portion of the extension surface and a third upper inclined surface connected to the upper portion of the second upper inclined surface. The diameter of the second upper inclined surface may increase upward, and the diameter of the third upper inclined surface may decrease upward.

The implant unit may include at least one or more gaps between the inner surface of the fixture and the outer surface of the intermediate structure. The gap may be filled with at least one or more of a biocompatible material, a lubricating material, and a polymer elastic material. The polymer elastic material may include at least one or more of polyvinylpyrrolidone (PVP), polyethylene glycol (PEG), polycaprolactone, gelatine, chitosan, hyaluronic acid, and alginate.

The cross-sectional shape of the second lower inclined surface may be a polygonal shape. The cross-sectional shape of the third upper inclined surface is a polygonal shape.

The lower portion of the intermediate structure may include a split rivet structure including a plurality of pieces apart from one another.

According to another aspect of the inventive concept, there is provided an implant unit including a fixture, which is assembled to an alveolar bone and includes a long hole formed in the depth-wise direction and having an opening on the top of the fixture; an intermediate structure, which is inserted to the long hole via the opening of the fixture; and an abutment assembled to the intermediate structure, wherein the long hole of the fixture includes a first lower inclined surface and an accommodating surface extended from the upper portion of the first lower inclined surface toward the opening of the fixture.

The first lower inclined surface may have a first lower inclined angle greater than 0° and below or equal to 20° with respect to vertical directions, and the accommodating surface may have an accommodation angle greater than 0° and below or equal to 20° with respect to vertical directions. The first lower inclined angle of the first lower inclined surface may be greater than the accommodation angle of the accommodating surface.

The fixture may further include a first upper inclined surface connected to the upper portion of the accommodating surface, and the first upper inclined surfaces may have a first upper inclined angle greater than 0° and below or equal to 20° with respect to vertical directions.

The intermediate structure may include a second lower inclined surface and an extension surface connected to the upper portion of the second lower inclined surface. The intermediate structure may include a second upper inclined surface connected to the upper portion of the extension surface, a stepped surface horizontally extending from the second upper inclined surface, and a third upper inclined surface extended upward from an end of the stepped surface.

The cross-sectional shape of the first upper inclined surface may be a polygonal shape. The cross-sectional shape of the third upper inclined surface may be a polygonal shape.

The intermediate structure may include a second bump, and the fixture may include a first bump for accommodating the second bump. The second bump may include a bump formed at the lower portion of the second lower inclined surface, and the first bump may include a groove formed at the lower portion of the first lower inclined surface to accommodate the bump. Alternatively, the first bump may include a bump formed at the lower portion of the first lower inclined surface, and the second bump may include a groove formed at the lower portion of the second lower inclined surface to accommodate the bump.

The implant unit may include a gap between a bottom surface of the abutment and the stepped surface of the intermediate structure. The gap may be filled with at least one or more of a biocompatible material, a lubricating material, and a polymer elastic material.

The implant unit may further include an assembling element that is rotation-assembled to the intermediate structure and the inner surface of the abutment. The assembling element may be a short assembling element having a relatively small length or a long assembling element having a relatively large length.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "module", a "block" or like, when used in the specification, represents a unit that processes at least one function or operation, and the unit or the like may be implemented by hardware or software or a combination of hardware and software.

It will be understood that when a layer is referred to as being "formed on," another layer, it can be directly formed on the other layer or intervening layers may be present therebetween. Likewise, when a material is referred to as being adjacent to another material, intervening materials may be present therebetween. In contrast, when a layer or material is referred to as being "directly" formed on, to another layer or material or as being "directly" adjacent to or contacting another layer or material, there are no intervening materials or layers therebetween.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings. However, they may be embodied in different forms and should not be construed as limited to the embodiments set forth herein. Rather, these embodiments are provided so that this disclosure will be thorough and complete, and will fully convey the scope of the disclosure to those skilled in the art.

Figure 1A:
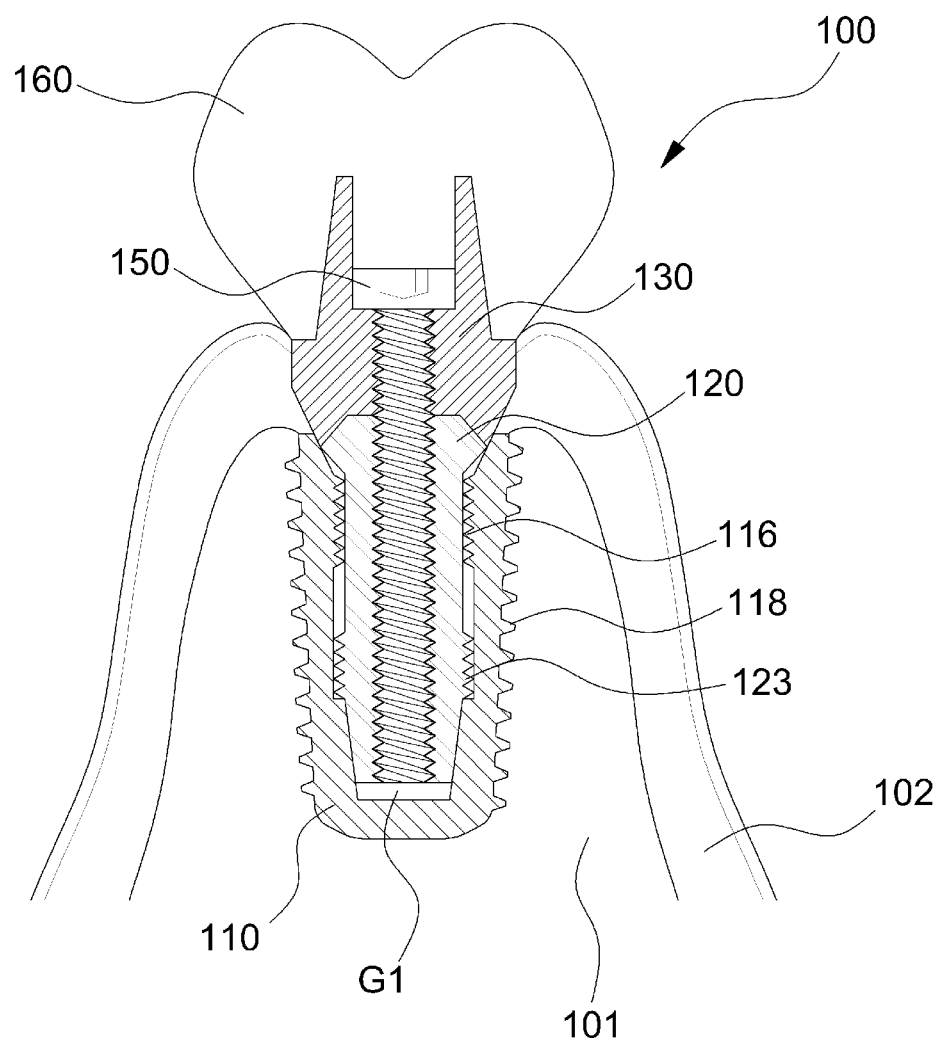
FIG. 1A is a sectional diagram showing an implant unit according to an embodiment of the present disclosure.
Figure 1B:
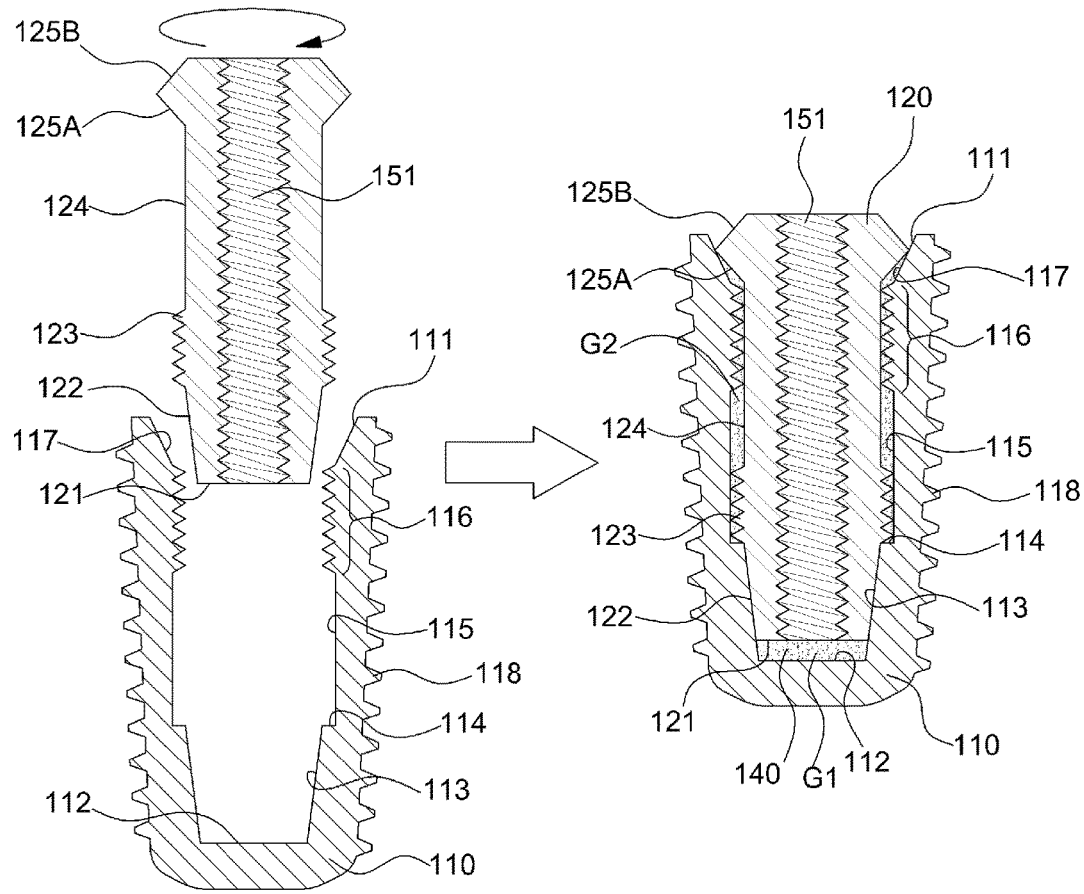
FIG. 1B is a sectional diagram showing how an intermediate structure is assembled to a fixture.

FIG. 1A is a sectional diagram showing an implant unit 100 according to an embodiment of the present disclosure, FIG. 1B is a diagram showing how an intermediate structure 120 is assembled to a fixture 110.

Referring to FIG. 1A, the implant unit 100 includes a fixture 110, which is assembled to an alveolar bone 101 and includes a long hole 111 formed in the depth-wise direction and having an opening on the top of the fixture 110, an intermediate structure 120, which is inserted to the long hole 111 via the opening of the fixture, and an abutment 130 assembled to the intermediate structure 120.

The fixture 110 is directly implanted to the alveolar bone 101 formed below a gum 102 and functions as a pillar. To this end, a plurality of screw threads 118 or bumps may be formed on the outer surface of the fixture 110 for integration with an alveolar bone 101. The fixture 110 may contain titanium, tungsten, aluminium, hafnium, niobium, tantalum, zirconium, platinum, or an alloy containing any one of the above-stated metals. However, the above-stated metals are merely examples, and the present disclosure is not limited thereto. Any of other non-corrosive metals with suitable strength and biocompatibility, non-metal ceramic artificial bone materials, or composite combinations thereof may be applied to the fixture 110. According to some embodiments, the fixture 110 may include a calcium phosphate-based ceramic coating layer, such as apatite hydroxide ($Ca_{10}(PO_4)_6(OH)_2$, HA), having excellent bioactivity on the surface of the fixture 110 to improve adhesion by promoting reactivity against the alveolar bone 101. According to another embodiment, a metal ceramic, such as $TiO_2$, $Ta_2O_5$, $Nb_2O_5$, $ZrO_2$, $SiO_2$, $RuO_2$, $MoO_3$, VO, $VO_2$, $V_2O_3$, $V_2O_5$, $CrO_2$, or $CrO_3$, may be coated on the fixture 110. The above-stated metals are merely examples, and one of ordinary skill in the art will understand that an arbitrary material capable of promoting osseointegration may be used as the coating material.

Referring to FIG. 1B, the fixture 110 includes a long hole 111 that is formed downward from the center of the top surface of the fixture 110 to a certain depth. The long hole 111 may include a bottom surface 112, and a first lower inclined surface 113 that is extended upward and increases upward the diameter of the corresponding portion of the long hole 111. Also, the long hole 111 may include a first stepped surface 114 (or a first horizontal surface) that horizontally is extended outward from or is connected to the first lower inclined surface 113. Also, the long hole 111 may include an accommodating surface 115 that is extended upward from or connected to the first stepped surface 114, a first structure 116 that is extended upward from or connected to the accommodating surface 115, and a first upper inclined surface 117 that is extended upward from or connected to the first structure 116. The above-stated accommodating surface 115 is merely an example, may be a tapered surface having an appropriate angle, a curved surface, or a combination thereof instead of a vertical surface, and may be a surface having any of various shapes for forming a suitable surface for accommodating a bumped pattern of a second structure 123 of the intermediate structure 120 as described below.

According to an embodiment, the intermediate structure 120 may include a bottom surface 121, which is, for example, a flat surface, a curved surface, or a surface having any of various shape, a second lower inclined surface 122 that is extended upward from or connected to the bottom surface 121 and increases upward the diameter of the corresponding portion of the intermediate structure 120, a second structure 123 that is extended upward from or connected to the second lower inclined surface 122, and an extension surface 124 that is extended upward from or connected to the second structure 123. The above-stated extension surface 124 is merely an example, may be a tapered surface having an appropriate angle, a curved surface, or a combination thereof instead of a vertical surface, and may be a surface having any of various shapes. According to an embodiment, the intermediate structure 120 may further include a second upper inclined surface 125A that is extended upward from or connected to the extension surface 124. Furthermore, an assembling groove 151 to be coupled to an assembling element 150 for assembling an abutment 130 to the intermediate structure 120 is formed at the center of the intermediate structure 120. The assembling element 150 may be a screw, for example.

According to an embodiment, the first structure 116 for coupling the intermediate structure 120 to the fixture 110 may be formed on the inner surface of the fixture 110, and the second structure 123 for coupling the intermediate structure 120 to the fixture 110 may be formed on the outer surface of the intermediate structure 120. When the fixture 110 is assembled to the intermediate structure 120, the first structure 116 and the second structure 123 are temporarily screw-coupled to each other via screw threads. Next, as the second structure 123 enters into the space formed by the accommodating surface 115, the first structure 116 and the second structure 123 are decoupled, and the intermediate structure 120 is guided straight into the long hole 111 of the fixture 110. Since the fixture 110 and the intermediate structure 120 are not firmly assembled, various irregular stresses occurring in a mount of a user, such as mastication of the food and teeth grinding, may be dispersed. Furthermore, the second lower inclined surface 122 of the intermediate structure 120 and the first lower inclined surface 113 of the fixture 110 form an inclined surface, the stresses applied in vertical directions or horizontal directions may be dispersed in various directions at wider area. Since the inclined surface formed by the first lower inclined surface 113 and the second lower inclined surface 122 is located at the lower portion of the implant unit 100, stress dispersion may occur at the lower portion of the implant unit 100. Similarly, various irregular stresses including stresses applied in vertical directions may be dispersed at the inclined surface formed by a second upper inclined surface 125A of the intermediate structure 120 and the first upper inclined surface 117 of the fixture 110.

A cross-section of the inclined surface perpendicular to the center axis CL may have a circular shape. Since the inclined surface formed by the second upper inclined surface 125A and the first upper inclined surface 117 is located at the upper portion of the implant unit 100, stress dispersion may occur at the upper portion of the implant unit 100 as described above. Therefore, when stresses are applied from the implant unit 100 to the alveolar bone 101, stresses may be transmitted in various directions via wider area due to the inclined surfaces formed at the upper portion and the lower portion of the implant unit 100. As a result, for example, a phenomenon that, when stresses are applied only from the upper portion of the implant unit contacting the alveolar bone 101 and the gum 102, the alveolar bone 101 is absorbed at the upper portion of the implant unit 100 may be prevented.

According to some embodiments, the first structure 116 and the second structure 123 may be other screw thread patterns or bumped patterns for guiding the intermediate structure 120 into the fixture 110, where the first structure 116 may be formed at the upper portion of the inner surface of the fixture 110, and the second structure 123 may be formed at the lower portion of the outer surface of the intermediate structure 120. A distance between the first structure 116 and the second structure 123 after the fixture 110 and the intermediate structure 120 are coupled to each other as shown in the right portion of FIG. 1B is greater than 0, thereby forming a certain gap to allow relative movements of the intermediate structure 120 and the fixture 110.

The long hole 111 of the fixture 110 includes the bottom surface 112, where a gap G1 may be formed between the bottom surface 112 of the fixture 110 and a bottom surface 121 of the intermediate structure 120. Furthermore, the inner surface of the fixture 110 and the outer surface of the intermediate structure 120 are a certain distance apart from each other, thereby forming a gap G2. According to an embodiment, the gaps G1 and G2 may be filled with at least one or more of a biocompatible material, a lubricating material, and a polymer elastic material 140. The polymer elastic material 140 enables elastic behavior when the fixture 110 and the intermediate structure 120 move in relation to each other, thereby enabling absorption and dispersion of stresses applied thereto. According to some embodiments, the polymer elastic material 140 may be polyvinylpyrrolidone (PVP), polyethylene glycol (PEG), polycaprolactone, gelatine, chitosan, hyaluronic acid, or alginate. However, the above-stated materials are merely examples, and it would have been obvious to one of ordinary skill in the art that the polymer elastic material 140 may be any of various materials for absorbing and dispersing stress.

The first lower inclined surface 113, which is extended upward from or connected to the bottom surface 112 constituting the long hole 111 of the fixture 110 and increases the diameter of the long hole 111 of the fixture 110, may closely contact the second lower inclined surface 122 of the intermediate structure 120, where the first lower inclined surface 113 and the second lower inclined surface 122 may slide with respect to each other. The first lower inclined surface 113 of the fixture 110 may 3-dimensionally absorb and disperse stress from the intermediate structure 120.

Furthermore, a cross-section of the second lower inclined surface 122 may have a circular shape, a polygonal shape (e.g., a triangular shape, a rectangular shape, a pentagonal shape, or a hexagonal shape), or an irregular shape. However, the above-stated shapes are merely examples, and one of ordinary skill in the art may easily apply various other cross-sectional shapes other than the above-stated shapes to the second lower inclined surface 122.

Figure 1C:
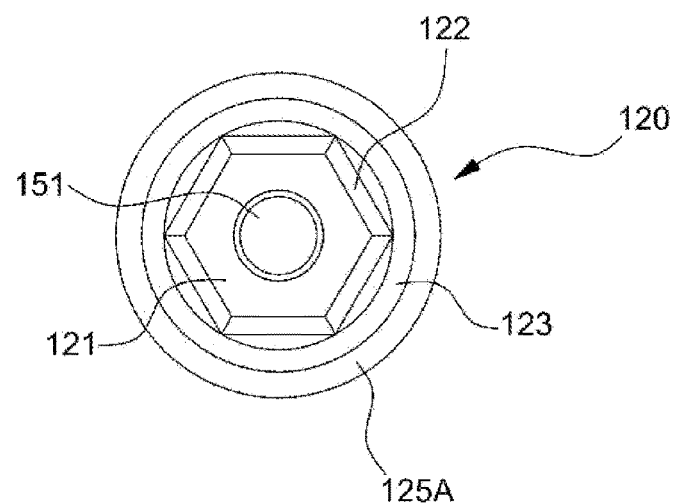
FIG. 1C is a plan view of the lower portion of an intermediate structure according to another embodiment.

FIG. 1C is a plan view of the lower portion of the intermediate structure 120 according to another embodiment. Referring to FIG. 1C, the shape of the bottom surface 121 of the intermediate structure 120 is not limited to a circular shape and may be a polygonal shape, such as a rectangular shape, a pentagonal shape, or a hexagonal shape, or an elliptical shape. FIG. 1C exemplifies the hexagonal bottom surface 121.

Figure 1D:
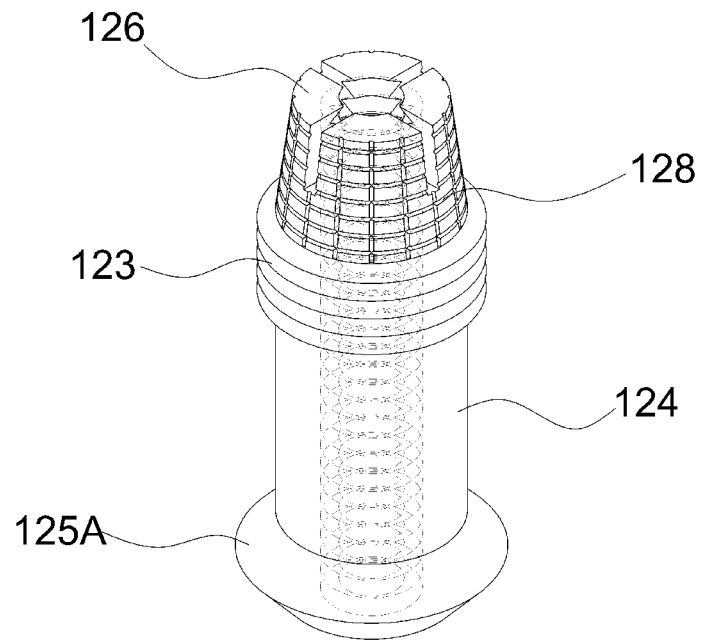
FIG. 1D is a perspective view of the lower portion of an intermediate structure according to another embodiment.
Figure 1E:
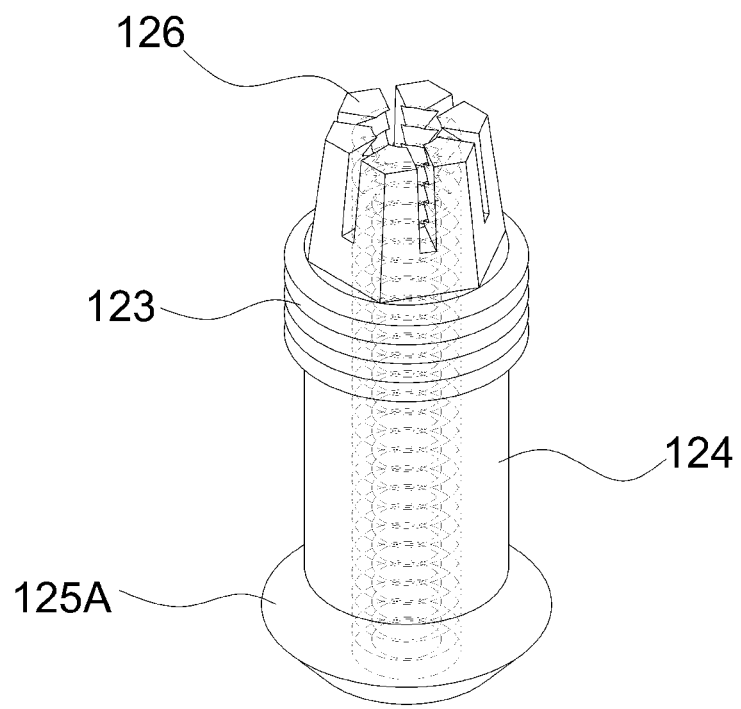
FIG. 1E is a perspective view of the lower portion of an intermediate structure according to another embodiment.

FIGS. 1D and 1E are perspective views of the lower portion of the intermediate structure 120 according to another embodiment.

Referring to FIG. 1D, a groove 128 may be formed on the second lower inclined surface 122 of the intermediate structure 120. As the polymer elastic material 140 may flow into the gap G1 formed adjacent to the bottom surface 112 of the long hole 111 via the groove 128, the gap G1 may be filled with the polymer elastic material 140 and absorb and disperse stress. The groove 128 may be formed on the second lower inclined surface 122 as a lattice-like pattern or a plurality of straight lines or curved lines a certain distance apart from one another. However, the above-stated shapes of the groove 128 are merely examples, and it would have been obvious to one of ordinary skill in the art that the groove 128 may have an arbitrary shape as long as the polymer elastic material 140 may flow to the bottom surface 112 via the groove 128.

Furthermore, referring to FIGS. 1D and 1E, the intermediate structure 120 may include a split rivet structure 126 including a plurality of pieces apart from one another at the lower portion of the intermediate structure 120. The split rivet structure 126 includes the assembling groove 151 therein to be coupled to the assembling element 150 for firm assembly between the intermediate structure 120 and the abutment 130. The split rivet structure 126 includes a plurality of pieces that are a certain distance apart from one another. As shown in FIG. 1D, the plurality of pieces may have arc-like shapes corresponding to two, three, four, five, or more equally divided portions of a circle. Furthermore, as shown in FIG. 1E, the plurality of pieces may have a shape corresponding to two, three, or more equally divided portions of a polygon, such as a rectangle, a pentagon, hexagon or a polygon with more vertices.

If the lower portion of the intermediate structure 120 includes the split rivet structure 126, while the intermediate structure 120 is being guided toward the bottom of the fixture 110 to be assembled to the fixture 110, the intermediate structure 120 may be slightly further moved in a vertical direction as the plurality of pieces of the split rivet structure 126 are closed toward the center axis CL, and thus stress may be reduced via absorption and dispersion. If necessary, if the assembling element 150 for coupling the abutment (130 of FIG. 1A) to the intermediate structure 120 is a screw and the abutment 130 and the intermediate structure 120 are coupled to each other via the screw, the lower portion of the screw moves to the lower portion of the intermediate structure 120 and fills the internal space of the intermediate structure 120. As a result, the plurality of pieces is limited from being closed, and thus a firm assembly may be provided between the intermediate structure 120 and the abutment 130. On the contrary, if the lower portion of the screw does not move to the split rivet structure 126 of the intermediate structure 120, the plurality of pieces of the split rivet structure 126 may be elastically deformed, and thus a vertical stress applied from the abutment 130 may be absorbed and/or reduced as the plurality of pieces are elastically deformed.

Referring back to FIG. 1B, the first stepped surface 114 that horizontally is extended outward from or is connected to the first lower inclined surface 113 of the fixture 110 may be formed. The first stepped surface 114 may absorb stress applied from the intermediate structure 120 in vertical directions and disperse the stress. Furthermore, the first stepped surface 114 may secure spaces in which the first structure 116 of the fixture 110 and the second structure 123 of the intermediate structure 120 protrude and secure a space via which the gap G2 formed between the fixture 110 and the intermediate structure 120 is filled with the polymer elastic material 140.

As described above, the polymer elastic material 140 filling the gaps G1 and G2, which are formed between the fixture 110 and the intermediate structure 120, and the intermediate structure 120 function like as the periodontal membrane of a natural tooth to protect the implant unit 100 and prevents absorption of the alveolar bone, and thus the implant unit 100 may function as a tooth immediately after being implanted. The periodontal membrane of a natural tooth refers to a connective tissue fibrous coat that interconnects a cement substance, which is formed between a tooth and the alveolar bone and has a thickness from about 50 μm to about 200 μm, and the alveolar bone. The periodontal membrane elastically fixes a tooth to the jaw bone and reduces a pressure generated by mastication of the food. Like as the natural periodontal membrane, the polymer elastic material 140 may function as an artificial periodontal membrane that provides firm and elastic assembly between the fixture 110 and the intermediate structure 120 inside the fixture 110 for stress dispersion.

The accommodating surface 115 that is extended upward from or connected to the first stepped surface 114 of the fixture 110 may be formed a certain distance apart from the second structure 123 that is extended upward from or connected to the second lower inclined surface 122 of the intermediate structure 120. According to an embodiment, the second structure 123 of the intermediate structure 120 couples the intermediate structure 120 to the fixture 110 and fixes the same, thereby preventing rotation of the intermediate structure 120 due to stress. According to an embodiment, the length of the accommodating surface 115 may be longer than that of the second structure 123.

The first structure 116 that is extended upward from or connected to the accommodating surface 115 of the fixture 110 may be a certain distance apart from the extension surface 124 of the intermediate structure 120. The first structure 116 of the fixture 110 may fix the intermediate structure 120, thereby preventing rotation of the intermediate structure 120 due to stress. The length of the extension surface 124 may be longer than that of the first structure 116.

The first upper inclined surface 117 that is extended upward from or connected to the first structure 116 of the fixture 110 and increases upward the diameter of the corresponding portion of the long hole 111 may be a certain distance apart from the second upper inclined surface 125 that is extended upward from or connected to the extension surface 124 of the intermediate structure 120. The second upper inclined surface 125A of the intermediate structure 120 is extended upward from or connected to the extension surface 124 and increases upward the diameter of the corresponding portion of the intermediate structure 120. Furthermore, a third upper inclined surface 125B of the intermediate structure 120 is extended upward from or connected to the second upper inclined surface 125A and decreases upward the diameter of the corresponding portion of the intermediate structure 120. The portion of the intermediate structure 120 at which the second upper inclined surface 125A and the third upper inclined surface 125B meet may closely contact or be apart from the first upper inclined surface 117 of the fixture 110.

Furthermore, the first upper inclined surface 117 may have a polygonal cross-section, such as a triangular cross-section, a rectangular cross-section, a pentagonal cross-section, or a hexagonal cross-section, and prevents rotation of the abutment 130. However, the above-stated polygonal shapes are merely examples, and it would have been obvious to one of ordinary skill in the art that an arbitrary polygonal shape for preventing rotation of the abutment 130 may be applied.

As described above, the intermediate structure 120 may be assembled to the long hole 111 of the fixture 110, so that the intermediate structure 120 and the fixture 110 may absorb and disperse stress transmitted from the abutment 130 and the crown 160 together. The intermediate structure 120 may be formed of any one selected from among titanium (Ti), surgical stainless steel, gold (Au), white ceramic zirconium (Zr), and a material equivalent thereto. However, the above-stated materials are merely examples, and it would have been obvious to one of ordinary skill in the art that an arbitrary material for absorbing and dispersing stress may be applied to the intermediate structure 120.

The upper portion of the intermediate structure 120 including the third upper inclined surface 125B may protrude more than the fixture 110, thereby securing an area for mounting the abutment 130. The abutment 130 may be assembled onto the upper portion of the intermediate structure 120. To prevent the abutment 130 mounted on the top of the intermediate structure 120 from being rotated and slipped, the upper portion of the intermediate structure 120 may secure an area for assembly of the abutment (130 of FIG. 1A), where the upper portion may be machined to have a polygonal shape, such as a hexagonal shape or a rectangular shape, when viewed from above.

According to an embodiment, the lower portion of the abutment 130 may include a groove area for accommodating the upper portion of the intermediate structure 120. If the upper portion of the intermediate structure 120 has a tapered shape with a width decreasing upward, the upper portion of the intermediate structure 120 increases a contact area between the groove area of the abutment 130 and the upper portion of the intermediate structure 120 and provides a tilted surface, thereby dispersing stress generated at the assembly between the lower portion of the abutment 130 and the upper portion of the intermediate structure 120 and reducing fatigue. As a result, the lifespan of the implant unit 100 may be increased and, during an implant surgery, the tilted surface may function as a guide for easy assembly between the lower portion of the abutment 130 and the intermediate structure 120.

The crown 160 or an artificial tooth is mounted on the abutment 130 mounted on the upper portion of the intermediate structure 120. The abutment 130 and the intermediate structure 120 may be firmly coupled to each other via the assembling element 150, such as a screw. The assembling groove 151 may be provided inside the intermediate structure 120, whereas the assembling element 150 may be screw-assembled into the assembling groove 151.

According to the above embodiment, the intermediate structure 120 enables the fixture 110 to function immediately as the fixture 110 is implanted. Furthermore, the gaps G1 and G2 formed between the fixture 110 and the intermediate structure 120 are filled with the polymer elastic material 140, thereby protecting an implant unit and an alveolar bone from harmful shocks from mastication of the food, teeth clenching, and teeth grinding.

Figure 2A:
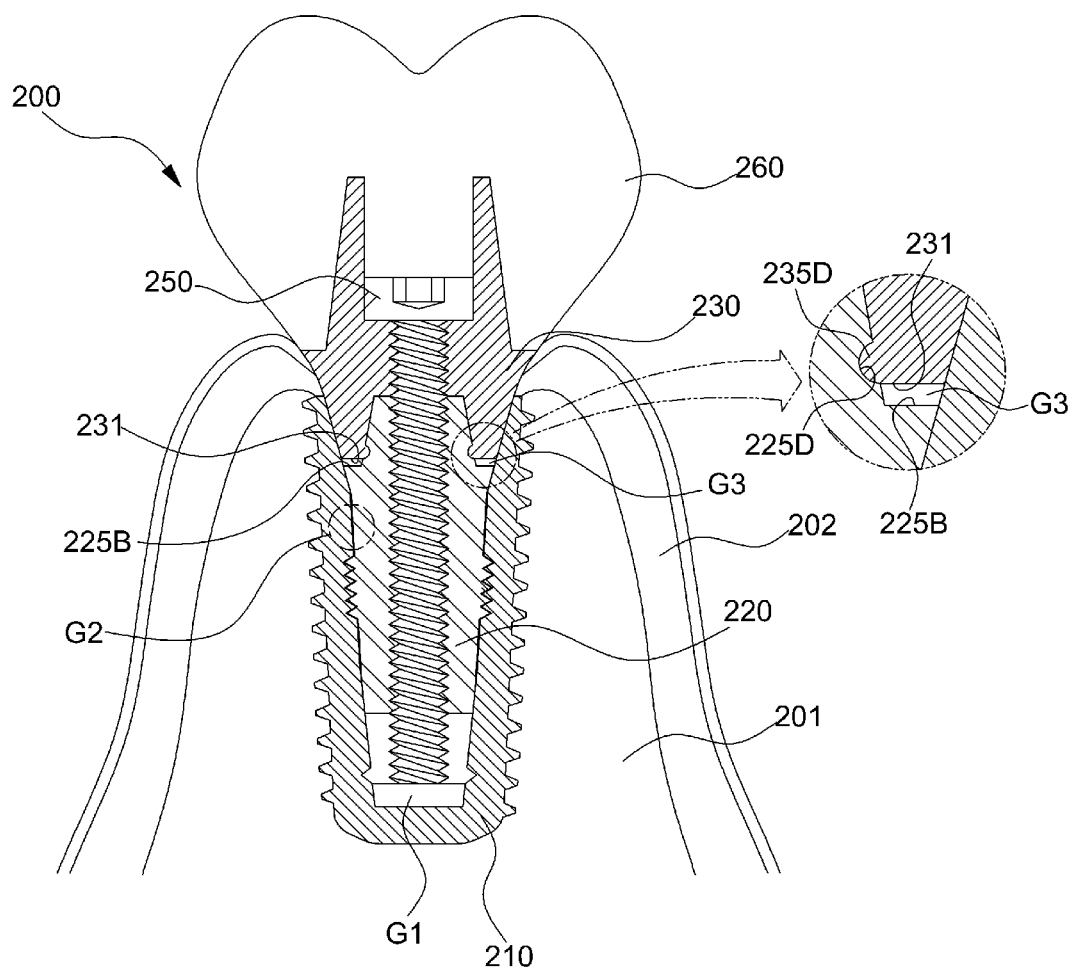
FIG. 2A is a sectional diagram of an implant unit according to another embodiment.
Figure 2B:
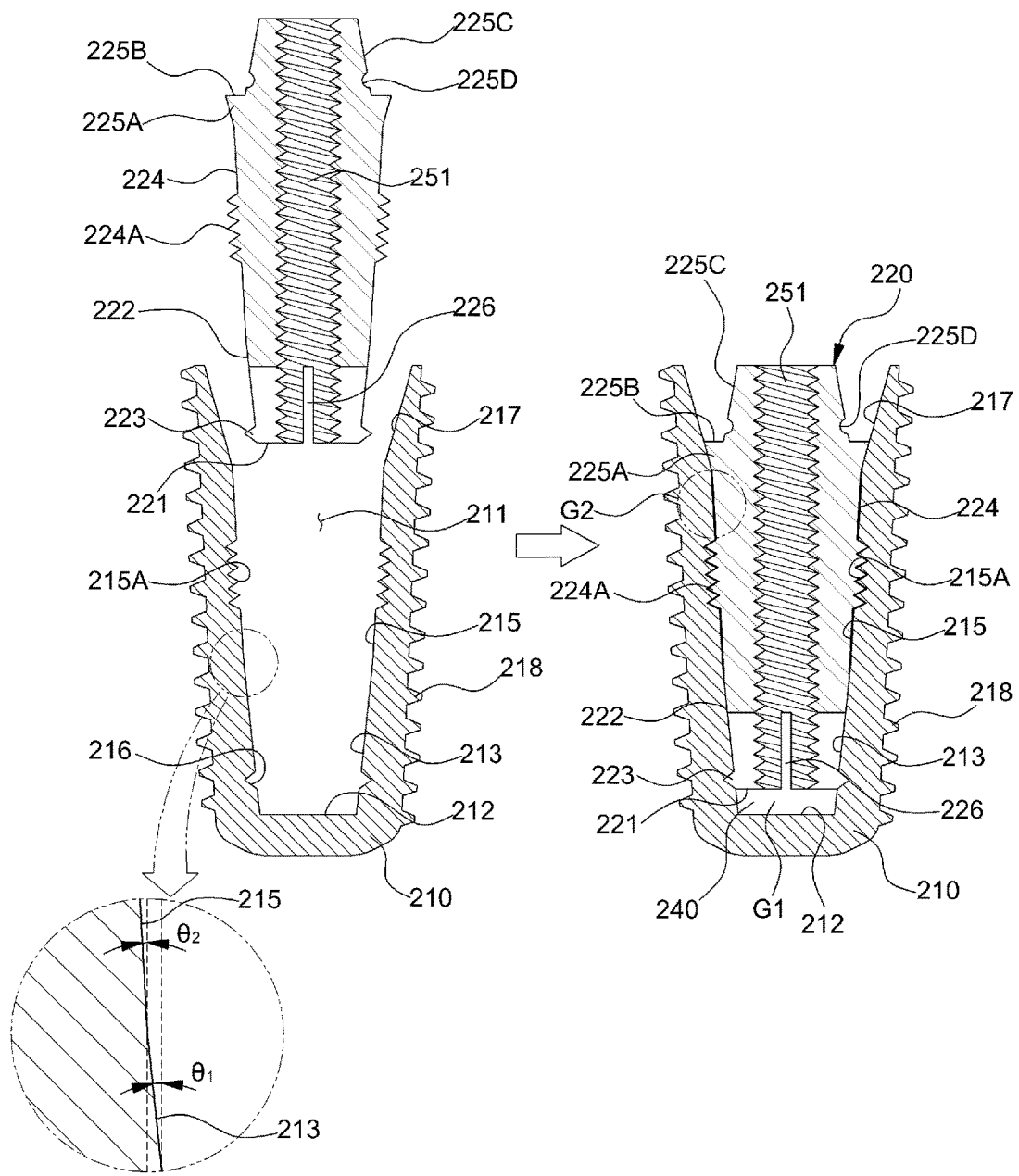
FIG. 2B is a sectional diagram showing how an intermediate structure is assembled to a fixture.

FIG. 2A is a sectional diagram of an implant unit 200 according to another embodiment, and FIG. 2B is a sectional diagram showing how an intermediate structure 220 is assembled to a fixture 210.

Referring to FIG. 2A, the implant unit 200 according to an embodiment includes a fixture 210, which is implanted to an alveolar bone 201 and includes a long hole 211 therein, the intermediate structure 220 inserted and assembled to the long hole 211 of the fixture 210, and an abutment 230 assembled to the intermediate structure 220.

The fixture 210 is directly implanted to the alveolar bone 201 formed below a gum 202 and functions as a pillar. To this end, a plurality of screw threads 218 or bumps may be formed on the outer surface of the fixture 210 for integration with an alveolar bone 201.

Referring to FIG. 2B, the fixture 210 includes a long hole 211 that is formed downward from the center of the top surface of the fixture 210 to a certain depth. The long hole 211 may include a bottom surface 212, a first lower inclined surface 213 that is extended upward from or connected to the bottom surface 212 and increases upward the diameter of the corresponding portion of the long hole 211, an accommodating surface 215 that is extended upward from or connected to the first stepped surface 214, and a first upper inclined surface 217 that is extended upward from or connected to the first structure 216. The accommodating surface 215 may be a tapered surface having an appropriate angle, a curved surface, or a combination thereof instead of a vertical surface, or may be a surface having any of various shapes for forming a suitable space for accommodating the intermediate structure 220 as described below.

For example, the first lower inclined surface 213 may have a first lower inclined angle greater than 0° and below or equal to 20° with respect to vertical directions. The accommodating surface 215 may have an accommodation angle greater than 0° and below or equal to 20° with respect to vertical directions. Accommodating surface screw threads 215A may be formed at the accommodating surface 215, such that the accommodating surface 215 is rotation-coupled to the intermediate structure 220. The accommodating surface screw threads 215A is formed at a location corresponding to a screw threads 224A formed at the intermediate structure 220. The first lower inclined angle of the first lower inclined surface 213 may be greater than the accommodation angle of the accommodating surface 215. As shown in FIG. 2B, the first lower inclined angle $\ominus 1$ of the first lower inclined surface 213 is greater than the accommodation angle $\ominus 2$ of the accommodating surface 215. However, the first lower inclined angle or the accommodation angle is merely an example, and the first lower inclined surface 213 and the accommodating surface 215 may be formed for various first bottom tilted angles or accommodation angles.

For example, the intermediate structure 220 may include a bottom surface 221, which is, for example, a flat surface, a curved surface, or a surface having any of various shape, a second lower inclined surface 222 that is extended upward from or connected to the bottom surface 221 and increases upward the diameter of the corresponding portion of the intermediate structure 220, and an extension surface 224 that is extended upward from or connected to the second lower inclined surface 222. The above-stated extension surface 224 may be a tapered surface having an appropriate angle, a curved surface, or a combination thereof and may be a surface having any of various shapes.

Since the intermediate structure 220 is accommodated in the above-stated fixture 210, the second lower inclined surface 222 is accommodated by the first lower inclined surface 213, and the extension surface 224 is accommodated by the accommodating surface 215. The extension surface screw threads 224A are formed on the extension surface 224 for rotation-coupling the extension surface 224 to the fixture 210. The extension surface screw threads 224A is formed at a location corresponding to that of the accommodating surface 215 formed at the fixture 210. Since the extension surface screw threads 224A is formed to be significantly smaller than the accommodating surface screw threads 215A, a significant gap is formed between the extension surface screw threads 224A and the accommodating surface screw threads 215A in order to accommodate sinking of the intermediate structure 220 that occurs while an implant unit is functioning. The second lower inclined surface 222 may have a second lower inclined angle greater than 0° and below or equal to 20° with respect to vertical directions. Furthermore, the extension surface 224 may have an extension angle greater than 0° and below or equal to 20° with respect to vertical directions. Particularly, the second lower inclined angle of the second lower inclined surface 222 may be greater than the extension angle of the extension surface 224. However, the second lower inclined angle or the extension angle is merely an example, and the second lower inclined surface 222 and the extension surface 224 may be formed for various second bottom tilted angles or extension angles.

The intermediate structure 220 may further include a second upper inclined surface 225A that is extended upward from or connected to the extension surface 224. Furthermore, the intermediate structure 220 includes a stepped surface 225B that horizontally is extended from the second upper inclined surface 225A and a third upper inclined surface 225C that is extended upward from an end of the stepped surface 225B. Furthermore, an assembling groove 251 to be coupled to an assembling element 250 for assembling an abutment 230 to the intermediate structure 220 is formed at the center of the intermediate structure 220. The assembling element 250 may be a screw, for example.

A first bump 216 for coupling the fixture 210 to the intermediate structure 220 may be formed at the lower portion of the assembling groove 251 of the fixture 210, whereas a second bump 223 for coupling the intermediate structure 220 to the fixture 210 may be formed at the lower portion of the intermediate structure 220. The first bump 216 may be a groove, whereas the second bump 223 may be a bump. As the bump 223 of the intermediate structure 220 is inserted to the groove 216 of the fixture 210, the fixture 210 and the intermediate structure 220 may be assembled to each other. According to another embodiment, a bump may be formed at the fixture 210 instead of a groove, a groove may be formed at the intermediate structure 220 instead of a bump, and thus the fixture 210 and the intermediate structure 220 may be coupled to each other via the bump and the groove. Since the fixture 210 and the intermediate structure 220 are not firmly assembled to each other, various irregular stresses occurring in a mount of a user, such as mastication of the food and teeth grinding, may be dispersed. Furthermore, when the bump and the groove of the intermediate structure 220 and the fixture 210 are assembled to each other, the 3-dimensional shape of the bump disperses weights applied in vertical directions to lateral directions, thereby reducing vertical stress. Furthermore, the second lower inclined surface 222 of the intermediate structure 220 and the first lower inclined surface 213 of the fixture 210 form an inclined surface, thereby dispersing stresses applied in vertical directions or horizontal directions to various directions at wider area. Since the inclined surface inclined surface formed by the first lower inclined surface 213 and the second lower inclined surface 222 is located at the lower portion of the implant unit 200, stress dispersion may occur at the lower portion of the implant unit 200. Similarly, various irregular stresses including stresses applied in vertical directions may be dispersed as vertical stress is converted to horizontal stress at the inclined surface formed by a second upper inclined surface 225A of the intermediate structure 220 and the first upper inclined surface 217 of the fixture 210. Since the inclined surface formed by the second upper inclined surface 225A and the first upper inclined surface 217 is located at the upper portion of the implant unit 200, stress dispersion may occur at the upper portion of the implant unit 200. Meanwhile, the second upper inclined surface 225A of the intermediate structure 220 is formed to have an inclined angle smaller than that of the first upper inclined surface 217 of the fixture 210, and thus vertical stress transmitted from the abutment 230 is transmitted to the center of the intermediate structure 220 and dispersed thereat. Therefore, when stresses are applied from the implant unit 200 to the alveolar bone 201, stresses may be transmitted in various directions via wider area due to the tilted interfaces formed at the upper portion and the lower portion of the implant unit 200. As a result, for example, a phenomenon that, when stresses are applied only from the upper portion of the implant unit contacting the alveolar bone 201 and the gum 202, the alveolar bone 201 is absorbed at the upper portion of the implant unit 200 may be prevented.

The long hole 211 of the fixture 210 includes the bottom surface 212, where a gap G1 may be formed between the bottom surface 212 of the fixture 210 and the bottom surface 221 of the intermediate structure 220. Furthermore, the inner surface of the fixture 210 (e.g., the accommodating surface) and the outer surface of the intermediate structure 220 (e.g., the extension surface) are a certain distance apart from each other, thereby forming a gap G2. According to an embodiment, the gaps G1 and G2 may be filled with a biocompatible material, a lubricating material, or a polymer elastic material 240. The biocompatible polymer elastic material 240 enables elastic behavior when the fixture 210 and the intermediate structure 220 move in relation to each other, thereby enabling absorption and dispersion of stresses applied thereto. According to some embodiments, the polymer elastic material 240 may be polyvinylpyrrolidone, (PVP), polyethylene glycol (PEG), polycaprolactone, gelatine, chitosan, hyaluronic acid, or alginate. However, the above-stated materials are merely examples, and it would have been obvious to one of ordinary skill in the art that the polymer elastic material 240 may be any of various materials for absorbing and dispersing stress.

The first lower inclined surface 213, which is extended upward from or connected to the bottom surface 212 constituting the long hole 211 of the fixture 210 and increases upward the diameter of the long hole 211 of the fixture 210, may closely contact the second lower inclined surface 222 of the intermediate structure 220, where the first lower inclined surface 213 and the second lower inclined surface 222 may slide with respect to each other. The first lower inclined surface 213 of the fixture 210 may 3-dimensionally absorb and disperse stress from the intermediate structure 220.

Figure 2C:
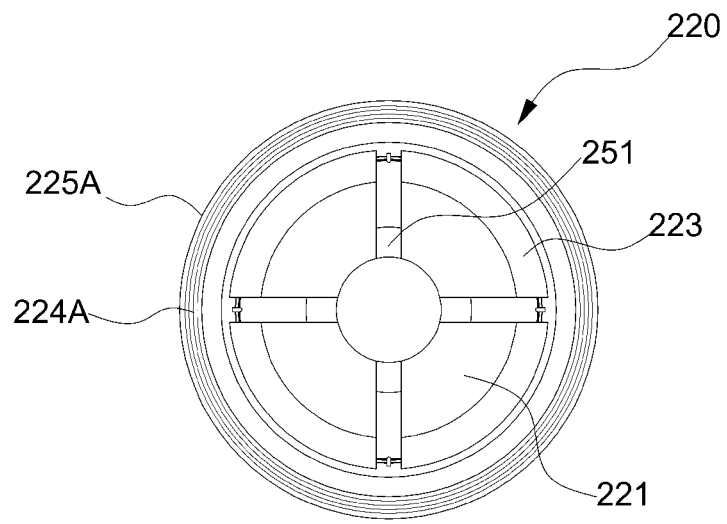
FIG. 2C is a plan view of the lower portion of an intermediate structure according to another embodiment.

FIG. 2C is a plan view of the lower portion of the intermediate structure 220 according to another embodiment. The shape of the bottom surface 221 of the intermediate structure 220 is not limited to a circular shape and may be a polygonal shape, such as a rectangular shape, a pentagonal shape, or a hexagonal shape, or an elliptical shape.

Figure 2D:
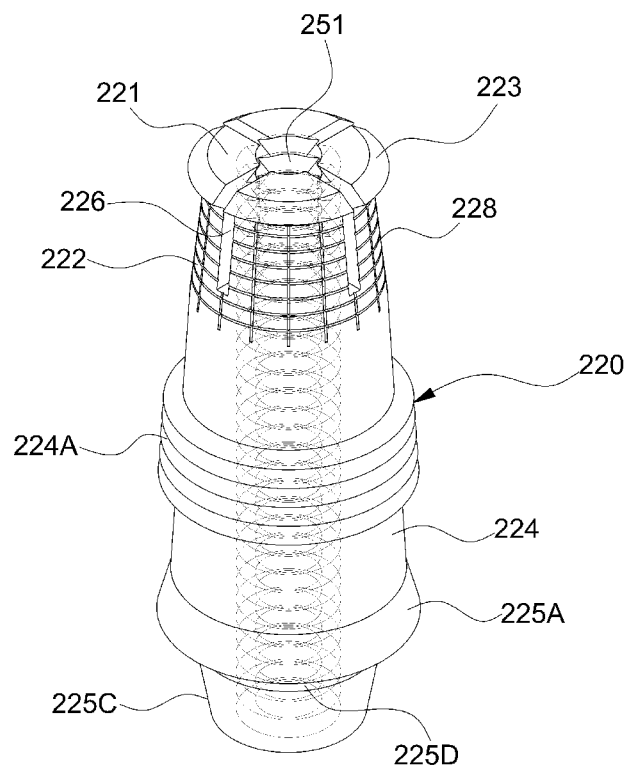
FIG. 2D is a perspective view of the lower portion of an intermediate structure according to another embodiment.

FIG. 2D is a perspective view of the lower portion of the intermediate structure 120 according to another embodiment. Referring to FIG. 2D, the intermediate structure 220 may include a split rivet structure 226 at the lower portion of the intermediate structure 220. The split rivet structure 226 includes the assembling groove 251 therein to be coupled to the assembling element 250 for firm assembly between the intermediate structure 220 and the abutment 230. The split rivet structure 226 includes a plurality of pieces that are a certain distance apart from one another. The plurality of pieces may have arc-like shapes corresponding to two, three, four, five, or more equally divided portions of a circle.

Referring to FIG. 2d, a groove 228 may be formed on the second lower inclined surface 222 of the intermediate structure 220. As the polymer elastic material 240 may flow into the gap G1 formed adjacent to the bottom surface 212 of the long hole 211 via the groove 228, the gap G1 may be filled with the polymer elastic material 240 and absorb and disperse stress. The groove 228 may be formed on the second lower inclined surface 222 as a lattice-like pattern or a plurality of straight lines or curved lines a certain distance apart from one another. However, the above-stated shapes of the groove 228 are merely examples, and it would have been obvious to one of ordinary skill in the art that the groove 228 may have an arbitrary shape as long as the polymer elastic material 240 may flow to the bottom surface 212 via the groove 228.

Figure 2E:
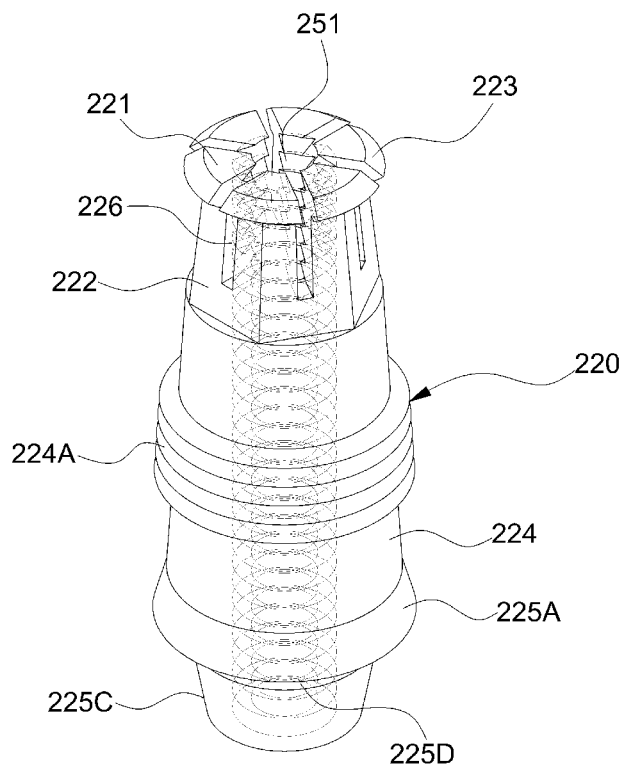
FIG. 2E is a perspective view of the lower portion of an intermediate structure according to another embodiment.

FIG. 2E is a perspective view of the lower portion of the intermediate structure 220 according to another embodiment. Referring to FIG. 2E, the plurality of pieces may have a shape corresponding to two, three, or more equally divided portions of a polygon, such as a rectangle, a pentagon, hexagon or a polygon with more vertices. If the lower portion of the intermediate structure 220 includes the split rivet structure 226, while the intermediate structure 220 is being guided toward the bottom of the fixture 210 to be assembled to the fixture 210, the intermediate structure 220 may be slightly further moved in a vertical direction as the plurality of pieces of the split rivet structure 226 are closed toward the center axis CL, and thus stress may be reduced via absorption and dispersion.

Referring back to FIG. 2B, the first upper inclined surface 217 of the fixture 210 may closely contact or be apart from the second upper inclined surface 225A of the intermediate structure 220. The second upper inclined surface 225A has a structure with a width increasing upward. Furthermore, the first upper inclined surface 217 may have a polygonal cross-section, such as a triangular cross-section, a rectangular cross-section, a pentagonal cross-section, or a hexagonal cross-section, and prevents rotation of the abutment 230.

As described above, the intermediate structure 220 may be assembled to the long hole 211 of the fixture 210, so that the intermediate structure 220 and the fixture 210 may absorb and disperse stress transmitted from the abutment 230 and the crown 260 together. Furthermore, the stepped surface 225B that horizontally is extended inward from or is connected to the second top sloped surface 225A of the intermediate structure 220 may be formed. The stepped surface 225B may absorb stress applied from the intermediate structure 220 in vertical directions and disperse the stress. Furthermore, the stepped surface 225B may secure spaces in which the first bump 216 of the fixture 210 and the second bump 223 of the intermediate structure 220 protrude and secure a space via which the gap G2 formed between the fixture 210 and the intermediate structure 220 is filled with the polymer elastic material 240.

Referring to FIG. 2A, a gap G3 may be formed between the bottom surface 231 of the abutment 230 and the stepped surface 225B of the intermediate structure 220. According to an embodiment, the third gap G3 may be filled with a biocompatible material, a lubricating material, or a polymer elastic material. The biocompatible polymer elastic material enables elastic behavior when the fixture 210 and the intermediate structure 220 move in relation to each other, thereby enabling absorption, and dispersion of stresses applied thereto.

The upper portion of the intermediate structure 220 including the third upper inclined surface 225C may protrude more than the fixture 210, thereby securing an area for mounting the abutment 230. The abutment 230 may be assembled onto the upper portion of the intermediate structure 220.

A groove 225D for coupling the fixture abutment 230 to the intermediate structure 220 may be formed below the third upper inclined surface 225C, whereas a bump 235D to be coupled to the groove 225D may be formed at a correspond portion of the abutment 230 coupled onto the third upper inclined surface 225C. Furthermore, for easy assembly of the abutment 230 to the intermediate structure 220, a groove may be formed at the abutment 230, whereas a bump may be formed at the intermediate structure 220. As the bump 235D of the abutment 230 is inserted to the groove 225D of the third upper inclined surface 225C, the intermediate structure 220 and the abutment 230 may be assembled to each other. According to another embodiment, a bump may be formed at the intermediate structure 220 instead of a groove, a groove may be formed at the abutment 230 instead of a bump, and thus the intermediate structure 220 and the abutment 230 may be coupled to each other via the bump and the groove. The abutment 230 may be prevented from being rotated by forming the first upper inclined surface 217 to have a polygonal shape. Furthermore, as the third upper inclined surface 225C is formed to have an inclined angle smaller than that of the first upper inclined surface 217, stress may be more concentrated at the intermediate structure 220.

The lower portion of the abutment 230 may include a groove area for accommodating the upper portion of the intermediate structure 220. If the upper portion of the intermediate structure 220 has a tapered shape with a width decreasing upward, the upper portion of the intermediate structure 220 increases a contact area between the groove area of the abutment 230 and the upper portion of the intermediate structure 220 and provides an inclined surface, thereby dispersing stress generated at the assembly between the lower portion of the abutment 230 and the upper portion of the intermediate structure 220 and reducing fatigue. As a result, the lifespan of the implant unit 200 may be increased and, during an implant surgery, the tilted surface may function as a guide for easy assembly between the bottom surface 231 of the abutment 230 and the intermediate structure 220.

The crown 260 or an artificial tooth is mounted on the abutment 230 mounted on the upper portion of the intermediate structure 220. The abutment 230 and the intermediate structure 220 may be firmly coupled to each other via the assembling element 250, such as a screw. The assembling groove 251 may be provided inside the intermediate structure 220, whereas the assembling element 250 may be screw-assembled into the assembling groove 251.

Figure 2F:
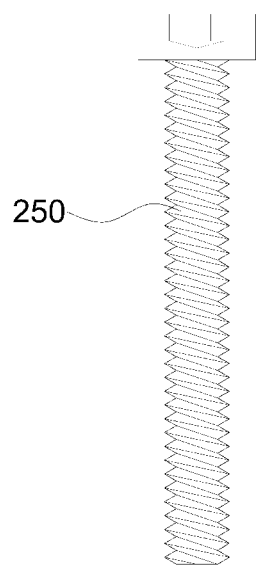
FIG. 2F is a plan view of an assembling element according to another embodiment.

FIG. 2F is a plan view of the assembling element 250 according to another embodiment. The assembling element 250 is an element for coupling the intermediate structure 220 to the abutment 230. If necessary, the assembling element 250 for coupling the abutment 230 to the intermediate structure 220 may be a screw. If the abutment 230 and the intermediate structure 220 are coupled to each other via the screw, the lower portion of the screw is extended to the lower portion of the intermediate structure 220. Therefore, as the screw limits the split rivet structure 226 from being closed, thereby providing a firm assembly between the intermediate structure 220 and the abutment 230. Here, if a groove is formed at the lower portion of the long hole 211 of the fixture 210 as the first bump 216 for coupling the fixture 210 to the intermediate structure 220 and a bump is formed at the lower portion of the intermediate structure 220 as the second bump 223 for coupling the intermediate structure 220 to the fixture 210, the lower portion of the screw is extended to the lower portion of the intermediate structure 220, and thus the bump may be firmly assembled to the groove. Meanwhile, if the lower portion of the screw does not extend to the split rivet structure 226 of the intermediate structure 220, the plurality of pieces of the split rivet structure 226 may be elastically deformed as described above, and thus a vertical stress applied from the abutment 230 may be absorbed and/or reduced as the plurality of pieces are elastically deformed.

According to the above embodiment, the intermediate structure 220 enables the fixture 210 to function immediately as the fixture 210 is implanted. Furthermore, the gaps G1 and G2 formed between the fixture 210 and the intermediate structure 220 and the third gap G3 formed between the intermediate structure 220 and the abutment 230 are filled with a polymer elastic material, thereby protecting an implant unit and an alveolar bone from harmful shocks from mastication of the food, teeth clenching, and teeth grinding.

Furthermore, according to an embodiment of the present disclosure, assembly between a fixture and an intermediate structure may be improved via a structure formed on the inner surface of the fixture for coupling the fixture to the intermediate structure. Furthermore, stress transmitted from the abutment to the fixture may be dispersed and/or absorbed by a gap formed between the fixture and the intermediate structure, thereby improving lifespan of an implant unit. Furthermore, in case of a patient with a thin alveolar bone due to absorption of the alveolar bone or teeth with a relatively small distance therebetween, even if an implant unit having the minimum diameter is applied, stress may be efficiently absorbed and dispersed by a gap formed between a fixture and an intermediate structure, and thus reliability equal to that of an implant unit having a relatively large size may be expected.

Furthermore, according to an embodiment of the present disclosure, an implant unit capable of increasing lifespan of the implant unit by preventing absorption of an alveolar bone by reducing stress at a tooth neck (where the implant unit meets the gum) may be provided. Furthermore, according to an embodiment of the present disclosure, since stress concentration may be resolved by forming the gap between the fixture and the intermediate structure, an implant unit having a relatively small diameter may be used. Therefore, an implant unit that may reduce additional surgeries, such as an additional bone grafting surgery, for reducing pain and recovery period after a surgery and surgery cost may be provided.

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:
1. An implant unit comprising:
 a fixture configured to assemble to an alveolar bone and comprises a long hole formed in a depth-wise direction and having an opening on a top of the fixture, wherein the long hole comprising:
 a bottom surface;
 a first lower inclined surface, which is extended from the bottom surface upwardly and having a first inclined angle;

an accommodating surface, which is extended from the first lower inclined surface upwardly and having a second inclined angle; and a first upper inclined surface, which is extended from a first structure upwardly and having a third inclined angle;

an intermediate structure, which is inserted into the long hole via the opening of the fixture, wherein the intermediate structure comprising:

a bottom surface;

a second lower inclined surface, which is extended from the bottom surface of the intermediate structure and having a shape being conformed to the first lower inclined surface;

a second structure, which is extended from the second lower inclined surface;

an extension surface, which is extended from the second structure; and a second upper inclined surface, which is extended from the extension surface and having a shape being conformed to the first upper inclined surface; and an abutment assembled to the intermediate structure;

wherein the first structure for coupling the fixture to the intermediate structure is formed on an inner surface of the fixture, wherein a lower portion of the intermediate structure comprises a split rivet structure including a plurality of pieces apart from one another, wherein a groove is formed on an outer surface of the pieces, wherein the groove is filled with a first polymer elastic material, wherein when the intermediate structure is assembled to the fixture, the second structure is temporarily coupled to the first structure and then decoupled from the first structure and guided straight into the long hole, wherein the implant unit further comprises a first gap formed between the bottom surface of the fixture and the bottom surface of the intermediate structure and a second gap formed between the accommodating surface and the extension surface when the fixture is completely assembled to the intermediate structure, wherein the first gap and the second gap are filled with at least one of a biocompatible material, a lubricating material, and a second polymer elastic material to disperse stresses applied thereto.

2. The implant unit of claim 1, wherein at least one of the first structure and the second structure comprises a screw thread pattern.

3. The implant unit of claim 1, wherein the intermediate structure comprises a third upper inclined surface connected to an upper portion of the second upper inclined surface.

4. The implant unit of claim 3, wherein the diameter of the second upper inclined surface increases upward, and the diameter of the third upper inclined surface decreases upward.

5. The implant unit of claim 1, wherein the first or second polymer elastic material comprises at least one or more of polyvinylpyrrolidone (PVP), polyethylene glycol (PEG), polycaprolactone, gelatine, chitosan, hyaluronic acid, and alginate.

6. The implant unit of claim 3, wherein a cross-sectional shape of at least one of the second lower inclined surface and the third upper inclined surface is a polygonal shape.

* * * * *